United States Patent
Rangabhatla Gunneswara Subramanya

(10) Patent No.: US 11,202,756 B2
(45) Date of Patent: Dec. 21, 2021

(54) ORAL DISINTEGRATING FILM COMPOSITIONS OF PARACETAMOL

(71) Applicant: SHILPA MEDICARE LIMITED, Raichur (IN)

(72) Inventor: Vara Prasad Rangabhatla Gunneswara Subramanya, Bengaluru (IN)

(73) Assignee: SHILPA MEDICARE LIMITED

( * ) Notice: Subject to any disclaimer, the term of this patent is extended or adjusted under 35 U.S.C. 154(b) by 0 days.

(21) Appl. No.: 16/618,159

(22) PCT Filed: Apr. 17, 2019

(86) PCT No.: PCT/IB2019/053158
§ 371 (c)(1),
(2) Date: Nov. 29, 2019

(87) PCT Pub. No.: WO2019/202521
PCT Pub. Date: Oct. 24, 2019

(65) Prior Publication Data
US 2021/0137831 A1    May 13, 2021

(30) Foreign Application Priority Data

Apr. 18, 2018 (IN) .............................. 201841014660

(51) Int. Cl.
| A61K 9/00 | (2006.01) |
| A61K 31/167 | (2006.01) |
| A61K 47/26 | (2006.01) |
| A61K 47/38 | (2006.01) |
| A61K 47/40 | (2006.01) |
| A61K 47/10 | (2017.01) |
| A61K 47/02 | (2006.01) |
| A61K 47/12 | (2006.01) |

(52) U.S. Cl.
CPC .......... *A61K 9/0056* (2013.01); *A61K 31/167* (2013.01); *A61K 47/02* (2013.01); *A61K 47/10* (2013.01); *A61K 47/12* (2013.01); *A61K 47/26* (2013.01); *A61K 47/38* (2013.01); *A61K 47/40* (2013.01)

(58) Field of Classification Search
CPC .... A61K 9/0056; A61K 31/167; A61K 47/02; A61K 47/10; A61K 47/12; A61K 47/26; A61K 47/38; A61K 47/40
USPC ........................................................ 514/630
See application file for complete search history.

(56) References Cited

U.S. PATENT DOCUMENTS 8,216,610 B2    7/2012 Roberts et al.

FOREIGN PATENT DOCUMENTS

| CN | 1679525 A | 10/2005 | |
| EP | 0421825 A1 | 4/1991 | |
| WO | WO-2013175511 A1 * | 11/2013 | ........... A61K 31/137 |
| WO | 2016024928 A1 | 2/2016 | |

OTHER PUBLICATIONS

Rutesh H. Dave et al., Development and Evaluation of High Loading Oral Dissolving Film of Aspirin and Acetaminophen, Journal of Pharmaceutical Sciences and Pharmacology vol. 1, 112-122, 2014, Arnold and Marie Schwartz College of Pharmacy and Health Sciences, Long Island University, Brooklyn, 11201, NY, USA.

Ikumi Ito et al., Preparation of an oral acetaminophen film that is expected to improve medication administration: Effect of polyvinylpyrrolidone on physical properties of the film, Drug Discoveries & Therapeutics. 2016; 10(3):156-162., Department of Practical Pharmacy, School of Pharmacy, Tokyo University of Pharmacy and Life Sciences, Tokyo, Japan; Department of Medicinal Therapy Research, Meiji Pharmaceutical University, Tokyo, Japan.

* cited by examiner

*Primary Examiner* — Kristin A Vajda

(57) ABSTRACT

The present invention relates to fast dissolving film composition comprising paracetamol or a pharmaceutically acceptable salt thereof as an active ingredient whose bitter taste is to be masked. More specifically, the present invention relates to a fast dissolving film composition containing paracetamol and taste masking agent; wherein taste masking agent is a mixture of sodium carbonate, citric acid and magnesium aluminometasilicate.

10 Claims, No Drawings

ORAL DISINTEGRATING FILM COMPOSITIONS OF PARACETAMOL

FIELD OF THE INVENTION

The present invention relates to fast dissolving film composition comprising paracetamol or a pharmaceutically acceptable salt thereof as an active ingredient whose bitter taste is to be masked. More specifically, the present invention relates to a fast dissolving film composition containing paracetamol and taste masking agent; wherein taste masking agent is a mixture of sodium carbonate, citric acid and magnesium aluminometasilicate.

Further, the present invention relates to an orally fast dissolving film composition containing of at least 40% w/w paracetamol based on the total weight of film composition and taste masking agent; wherein taste masking agent is a mixture of sodium carbonate, citric acid and magnesium aluminometasilicate.

BACKGROUND OF THE INVENTION

Paracetamol or Acetaminophen or 4'-hydroxyacetanilide is the most commonly used non-steroidal anti-inflammatory antipyretic analgesics for fever common cold or influenza bowl also used to relieve mild to moderate pain such as headaches, joint pain, migraine, toothache, muscle pain, neuralgia, dysmenorrhea. Moreover, paracetamol is the World Health Organization recommended the most effective and safe for children antipyretics for children with fever caused by the common cold or influenza have a good effect. Acetaminophen is chemically N-(4-Hydroxyphenyl) acetamide represented below.

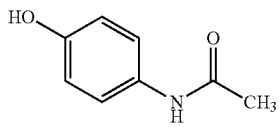

Products containing paracetamol are marketed in the form of tablet, capsule, suspension, effervescent, intravenous and intramuscular form. Paracetamol can be used in adults in the dose range of 500 mg to 1000 mg. The maximum daily dose for adults is 4000 mg. Paracetamol is recommended as the first-line drug for geriatric patients over 50 years old and for the pain and aches seen in influenza.

As well as the preferred route of paracetamol administration is oral, paracetamol is also well-known with its bitter taste. Paracetamol characteristic feature is its searing taste and leaving an unpleasant taste in the throat after swallowing. In the case of contact with mouth or throat mucosa, an unpleasant taste is felt. There is a need to mask/, inhibit the bitter taste of paracetamol given in disintegrated form during oral use such as syrup, effervescent tablet, oral disintegrating tablet. Even today, there is patient's complication about bitter taste left in mouth or throat after administrating paracetamol effervescent tablet. It is mentioned that even paracetamol syrups are having strong bitter taste couldn't mask by sweetening agents.

Oral dissolving films are gaining interest as an alternative of fast dissolving tablets. The films are designed to dissolve upon contact with a wet surface, such as the tongue, within a few seconds, meaning the consumer can take the product without need for additional liquid. This convenience provides both a marketing advantage and increased patient compliance. As the drug is directly absorbed into systemic circulation, degradation in gastrointestinal tract and first pass effect can be avoided. These points make this formulation most popular and acceptable among pediatric and geriatric patients and patients with fear of choking. Over-the-counter films for pain management and motion sickness are commercialized in the US markets.

The oral route is one of the most preferred routes of drug administration as it is more convenient, cost effective, and ease of administration lead to high level of patient compliance. The oral route is problematic because of the swallowing difficulty for pediatric and geriatric patients who have fear of choking. Patient convenience and compliance oriented research has resulted in bringing out safer and newer drug delivery systems. Recently, fast dissolving drug delivery systems have started gaining popularity and acceptance as one such example with increased consumer choice, for the reason of rapid disintegration or dissolution, self-administration even without water or chewing as to overcome swallowing difficulties associated with tablets and capsules for pediatric and geriatric patients. The surface of buccal cavity comprises of stratified squamous epithelium which is essentially separated from the underlying tissue of lamina propria and submucosa by an undulating basement membrane. It is interesting to note that the permeability of buccal mucosa is approximately 4-4,000 times greater than that of the skin, but less than that of the intestine.

An ideal fast dissolving delivery system should have the following properties: High stability, transportability, ease of handling and administration, no special packaging material or processing requirements, no water necessary for application, and a pleasant taste. Therefore, they are very suitable for pediatric and geriatric patients; bedridden patients; or patients suffering from dysphagia, parkinson's disease, Mucositis, or vomiting. Formulation of fast dissolving buccal film involves material such as strip-forming polymers, plasticizers, active pharmaceutical ingredient, sweetening agents, saliva stimulating agent, flavoring agents, coloring agents, stabilizing and thickening agents, permeation enhancers, and superdisintegrants.

U.S. Pat. No. 8,216,610 discloses the swallow formulation comprising paracetamol which facilitates the rapid delivery of paracetamol into the circulatory system following oral administration.

Patent NO. EP0421825 discloses the rally administrable solution comprising an analgesic as active ingredient and a solvent therefor which solvent contains polyethylene glycol.

PCT application NO. WO2016024928 discloses the taste masked oral pharmaceutical formulations where active ingredient is paracetamol and metallic salts are used.

Patent application CN1679525 discloses the acetaminophen orally disintegrating tablet.

Rutesh H. Dave et al. (Development and evaluation of high loading oral dissolving film of aspirin and acetaminophen) discloses the develop and evaluate physicochemical properties of acetaminophen and aspirin orally disintegrating strips with high loading dose.

Ikumi Ito et al, (Preparation of an oral acetaminophen film that is expected to improve medication administration: Effect of polyvinylpyrrolidone on physical properties of the film) discloses the effect of polyvinylpyrrolidone (PVP) on a film containing carboxymethyl cellulose sodium (CMC) as a matrix to improve surface roughness caused by drug recrystallization. Acetaminophen (AA) was used as the model drug.

Oral disintegrating film as disclosed in above prior art does not provide the desirable film properties with paracetamol that have high drug loading and further whose bitter taste is masked. Bitter taste masking of an active ingredient inevitably leads to poor physical properties and brittleness.

Therefore, present invention aims to provide oral disintegrating film and process for manufacturing the same to mask the bitterness of paracetamol with high drug loading. It relates more specifically oral disintegrating film containing paracetamol and taste masking agent.

SUMMARY OF THE INVENTION

In one object, the present invention provides herein, oral disintegrating film composition consisting essentially of a therapeutically effective amount of paracetamol or pharmaceutically acceptable salts thereof and an excipient that facilitates oral administration, and methods of use thereof for antipyretic for children.

It is an object of the present invention to provide fast dissolving film composition including at least of about 40.0% w/w of paracetamol based on the total weight of the film composition. The high dose of paracetamol is not loaded in film formulations of the prior art with the total weight of film composition as it causes a serious problem in the brittleness of the film. Based on this reason, it is an object of the present invention to provide fast dissolving film composition that is free from the problem of brittleness even when a high dose of paracetamol of more than 100 mg is loaded. Further the present inventors have founded that even when at least 40.0 % w/w of paracetamol is loaded and the problem of brittleness is solved, the medication compliance of patient upon administration is greatly deteriorated by ineffective masking of the bitter taste of the paracetamol. Considering this finding, it is another object of the present invention to provide a taste masking agent specifically designed to produce to desired formulation.

Particularly, it is an object of the present invention to provide a fast dissolving film composition of paracetamol whose bitter taste is masked by a specific taste masking agent and/or a mixture of specific taste masking agents. Furthermore, it is an object of the present invention to provide a pharmaceutical composition that has good ability to form an orally fast dissolving film composition comprising paracetamol and or a pharmaceutically acceptable salt thereof as an active ingredient whose bitter taste is masked by a mixture of specific taste masking agents.

It is a final object of the present invention to provide a fast dissolving film composition comprising of at least 40.0% w/w of paracetamol or a pharmaceutically acceptable salt thereof whose bitter taste is masked by a taste masking agent, wherein taste masking agent is mixture of sodium carbonate, citric acid and magnesium aluminometasilicate. Further the present invention is of technical significance in providing a fast dissolving film composition in which at least 40.0% w/w of paracetamol is loaded and the bitter taste of paracetamol is masked without causing any problem in film-forming ability.

DETAILED DESCRIPTION OF THE INVENTION

The present invention provides herein, compositions consisting essentially of a therapeutically effective amount of paracetamol and pharmaceutically acceptable excipients that facilitates oral administration and process for manufacturing the same.

In a preferred embodiment, the pharmaceutical composition of the invention is oral disintegrating film or a fast dissolving film composition.

In the most preferred embodiment, the pharmaceutical oral disintegrating film composition comprising paracetamol and pharmaceutically acceptable excipients.

The present invention discloses a fast dissolving film composition comprising paracetamol or a pharmaceutically acceptable salt thereof and a taste masking agent wherein paracetamol or a pharmaceutically acceptable salt thereof is at least 100 mg or at least 40.0% w/w by weight with respect to the total weight of the film.

Paracetamol is preferably used in a pharmaceutical oral disintegrating film/fast dissolving film composition of about 40.0% w/w to about 60.0% w/w based on the total weight of the composition. More preferable concentration of paracetamol in the composition is about 45.0% w/w to about 55.0% w/w by total weight of the composition and most preferable is of about 45.0% w/w to about 50.0% w/w based on the total weight of film composition.

In embodiments of the invention, the present invention relates to a fast dissolving film composition comprising paracetamol, solubilizer, disintegrant and a taste masking agent.

In embodiments of the invention, the present invention relates to a fast dissolving film composition comprising paracetamol, solubilizer, disintegrant and a taste masking agent, when the ratio of solubilizer and disintegrant is of about 1:3 to about 3:1.

The solubilizer is selected from the group consisting of benzyl alcohol, hydroxypropyl-β-cyclodextrin, polyvinylpyrrolidone, and sulfobutylether-β-cyclodextrin. Preferably, the solubilizer selected is hydroxypropyl-β-cyclodextrin. Hydroxypropyl-β-cyclodextrin preferably used in the pharmaceutical oral disintegrating film/fast dissolving film composition is of about 0.1% w/w to about 10.0% w/w based on the total weight of the composition. Most preferably, hydroxypropyl-β-cyclodextrin used in the composition of about 1.0% w/w to about 5.0% w/w based on total weight of the composition.

The disintegrant is selected from the group consisting of sodium starch glycolate, pregelatinized starch, carboxymethyl cellulose, and silicified microcrystalline cellulose and combinations thereof. Preferably disintegrant used in the composition is silicified microcrystalline cellulose. Silicified microcrystalline preferably used in the pharmaceutical oral disintegrating film/fast dissolving film composition is of about 1.0% w/w to about 20.0% w/w based on the total weight of the composition. More preferably, silicified microcrystalline cellulose used in the composition of about 5.0% w/w to about 15.0% w/w based on total weight of the composition and most preferably of about 5.0% w/w to about 10.0% w/w based on total weight of the composition.

The taste masking agent is selected from the group consisting of sodium carbonate, citric acid and magnesium aluminometasilicate. The taste masking agent is mixture of sodium carbonate, citric acid and magnesium aluminometasilicate in the ratio of 1:4.5:7.5.

The taste masking agent mixture consists of about 0.1% w/w to about 0.5% w/w sodium carbonate, about 0.5% w/w to about 1.0 w/w citric acid and about 0.5% w/w to about 2.0% w/w magnesium aluminometasilicate based on total weight of film composition.

In embodiments of the invention, the present invention relates to a fast dissolving film composition comprising
a) paracetamol or pharmaceutically acceptable salt thereof;

b) solubilizer selected from the group consisting of benzyl alcohol, hydroxypropyl-β-cyclodextrin, polyvinylpyrrolidone, and sulfobutylether-β-cyclodextrin;
c) disintegrant selected from the group consisting of sodium starch glycolate, pregelatinized starch, carboxymethyl cellulose, and silicified microcrystalline cellulose; and
d) taste masking agent; wherein taste masking agent is a mixture of sodium carbonate, citric acid and magnesium aluminometasilicate.

In another embodiment of the invention, the present invention relates to a fast dissolving film composition consisting essentially of
a) paracetamol or pharmaceutically acceptable salt thereof;
b) solubilizer selected from the group consisting of benzyl alcohol, hydroxypropyl-β-cyclodextrin, polyvinylpyrrolidone, and sulfobutylether-β-cyclodextrin;
c) disintegrant selected from the group consisting of sodium starch glycolate, pregelatinized starch, carboxymethyl cellulose, and silicified microcrystalline cellulose; and
d) taste masking agent; wherein taste masking agent is a mixture of sodium carbonate, citric acid and magnesium aluminometasilicate.

In further embodiments of the invention, the present invention relates to a fast dissolving film composition comprising of
a) at least 40% w/w of paracetamol; and
b) taste masking agent; wherein taste masking agent is a mixture of sodium carbonate, citric acid and magnesium aluminometasilicate.

In another embodiment of the invention, the present invention relates to a fast dissolving film composition consisting essentially of
a) at least 40% w/w of paracetamol; and
b) taste masking agent; wherein taste masking agent is a mixture of sodium carbonate, citric acid and magnesium aluminometasilicate.

In embodiments of the invention, the present invention relates to the fast dissolving oral film composition further comprising, polymer, plasticizer, sweetening agents, and at least one excipient selected from colouring agents and flavoring agents.

In embodiments of the invention, polymers used in the invention are selected from the group consisting of hydroxypropyl methylcellulose, ethyl cellulose, hydroxypropyl cellulose, polyvinyl alcohol and cellulose acetate phthalate and combinations thereof. Preferably, the polymer used in the present invention is hydroxylpropyl methyl cellulose (HPMC E15). Hydroxylpropyl methyl cellulose preferably used in the pharmaceutical oral disintegrating film composition is of about 10.0% w/w to about 25.0% w/w based on the total weight of the composition. More preferably hydroxypropyl methylcellulose used in the present invention is about 15.0% w/w to about 25.0% w/w hydroxypropyl methylcellulose and most preferably about 12.0% w/w to about 20.0% w/w based on total weight of the composition.

In embodiments of the invention, plasticizers used in the present invention are selected from the group consisting of polyethylene glycol, diethyl phthalate, propylene glycol and glycerol and combinations thereof. Preferably, the plasticizer used in the present invention is glycerol. Glycerol preferably used in the pharmaceutical oral disintegrating film composition is of about 0.1% w/w to about 10.0% w/w based on the total weight of the composition. Most preferably, glycerol is used in the composition of about 1.0% w/w to about 5.0% w/w based on total weight of the composition.

In embodiments of the invention, sweetening agents are selected from the group consisting of aspartame, sucralose, dextrose, fructose, ammonium glycyrrhizinate, maltose, mannitol, sorbitol and xylitol and/or combinations thereof. Preferably, the sweetening agent used in the present invention is a mixture of sucralose and xylitol. The pharmaceutical composition comprises a mixture of xylitol and sucralose in a ratio of about 3:1 to about 1:3 as the sweetening agent. More preferably sweetening agent mixture consists of about 3% w/w to about 5% w/w sucralose and about 1.0% w/w to about 3% w/w of xylitol based on the total weight of film composition.

Examples of the flavour agents are selected from the group consisting of peppermint flavour, cooling flavour (menthol), flavour oils, flavouring aromatic oil, peppermint oil, clove oil, bay oil, anise oil, eucalyptus oil thyme oil, oil of bitter almonds. Flavouring agents include, vanilla, chocolate flavour, citrus oils, fruit essences, and any combinations thereof. Preferably, the flavour agents are selected from menthol (polo mint) and chocolate flavour. Flavour agents preferably used in the pharmaceutical oral disintegrating film composition of about 5% to about 20% based on the total weight of the composition.

Examples of the colouring agent are selected from the group consisting of sunset yellow, amaranth, red iron oxide, natural juice concentrates, pigments and opacifying agents such as titanium oxide, silicon dioxide and zinc oxide, solid choco color and any combinations thereof. Preferably, the coloring agent is selected from solid choco color. Colouring agent preferably used in the pharmaceutical oral disintegrating film composition of about 0.001% to about 0.1% based on the total weight of the composition. Most preferably, colouring agent is used in the composition of about 0.01% to about 0.08% based on total weight of the composition.

In embodiments of the invention, the present invention relates to a fast dissolving film composition comprising of
a) about 45.0% w/w to about 50.0% w/w paracetamol based on total weight of film composition;
b) about 15.0% w/w to about 25.0% w/w hydroxypropyl methylcellulose based on total weight of film composition;
c) about 1.0% w/w to about 5.0% w/w hydroxypropyl β-cyclodextrin based on total weight of film composition;
d) about 5.0% w/w to about 10.0% w/w silicified microcrystalline cellulose based on total weight of film composition;
e) tasting masking agent mixture consisting about 0.1% w/w to about 0.5% w/w sodium carbonate, about 0.5% w/w to about 1.0 w/w citric acid and about 0.5% w/w to about 2.0% w/w magnesium aluminometasilicate based on total weight of film composition;
f) sweetening agent mixture consisting about 3% w/w to about 5% w/w sucralose and about 1.0% w/w to about 3% w/w of xylitol based on the total weight of film composition;
g) about 1.0% w/w to about 5.0% w/w of glycerol based on the total weight of film composition; and
h) at least one excipient selected from coloring agents and flavoring agents.

In further embodiments of the invention, the present invention relates to a fast dissolving film composition consisting essentially of
a) about 45.0% w/w to about 50.0% w/w paracetamol based on total weight of film composition;

b) about 15.0% w/w to about 25.0% w/w hydroxypropyl methylcellulose based on total weight of film composition;

c) about 1.0% w/w to about 5.0% w/w hydroxypropyl β-cyclodextrin based on total weight of film composition;

d) about 5.0% w/w to about 10.0% w/w silicified microcrystalline cellulose based on total weight of film composition;

e) tasting masking agent mixture consisting about 0.1% w/w to about 0.5% w/w sodium carbonate, about 0.5% w/w to about 1.0 w/w citric acid and about 0.5% w/w to about 2.0% w/w magnesium aluminometasilicate based on total weight of film composition;

f) sweetening agent mixture consisting about 3% w/w to about 5% w/w sucralose and about 1.0% w/w to about 3% w/w of xylitol based on the total weight of film composition;

g) about 1.0% w/w to about 5.0% w/w of glycerol based on the total weight of film composition; and h) at least one excipient selected from coloring agents and flavoring agents.

In another embodiment of the invention, the present invention relates to a fast dissolving film composition consisting of a) about 45.0% w/w to about 50.0% w/w paracetamol based on total weight of film composition;

b) about 15.0% w/w to about 25.0% w/w hydroxypropyl methylcellulose based on total weight of film composition;

c) about 1.0% w/w to about 5.0% w/w hydroxypropyl β-cyclodextrin based on total weight of film composition;

d) about 5.0% w/w to about 10.0% w/w silicified microcrystalline cellulose based on total weight of film composition;

e) tasting masking agent mixture consisting about 0.1% w/w to about 0.5% w/w sodium carbonate, about 0.5% w/w to about 1.0 w/w citric acid and about 0.5% w/w to about 2.0% w/w magnesium aluminometasilicate based on total weight of film composition;

f) sweetening agent mixture consisting about 3% w/w to about 5% w/w sucralose and about 1.0% w/w to about 3% w/w of xylitol based on the total weight of film composition;

g) about 1.0% w/w to about 5.0% w/w of glycerol based on the total weight of film composition; and h) at least one excipient selected from coloring agents and flavoring agents.

It is desirable that the oral film formulation of the present invention is formed into a thin film while maintaining tensile strength and toughness at desired levels.

In one embodiment, the oral film formulation of the present invention has a thickness of about 50 μm to about 1500 μm. The oral film formulation of the present invention has a size of about 1 cm$^2$ to about 12 cm$^2$, preferably 2 cm$^2$ to about 10 cm$^2$.

The following examples are provided to illustrate the present invention. It is understood, however, that the invention is not limited to the specific conditions or details described in the examples below. The examples should not be construed as limiting the invention as the examples merely provide specific methodology useful in the understanding and practice of the invention and its various aspects. While certain preferred and alternative embodiments of the invention have been set forth for purposes of disclosing the invention, modification to the disclosed embodiments can occur to those who are skilled in the art.

EXAMPLE 1

Oral Disintegrating Film with Following Solvent System Composition

| S. No. | Ingredients | w/w % |
| --- | --- | --- |
| 1 | Paracetamol | 40%-60% |
| 2 | Sucralose | 0.33%-4% |
| 3 | Prosolv ODT G2 | 1%-20% |
| 4 | Hydroxypropyl Betacyclodextrin | 0.1%-10% |
| 5 | Ammonium Glycyrrhizinate | 0.33%-4% |
| 6 | Xylitol | 0.33%-4% |
| 7 | Hydroxylpropyl methylcellulose E15 | 10%-25% |
| 8 | Glycerol | 0.1%-10% |
| 9 | Chocolate Flavor | 2.5%-10% |
| 10 | Cooling Agent Flavor | 2.5%-10% |
| 11 | Sodium Carbonate | 0.05%-5% |
| 12 | Citric Acid | 0.05%-5% |
| 13 | Solid Choco Colour | 0.001%-0.1% |
| 14 | Purified Water | Q.S to 100% |
|  | Total strip weight | 100.00% |

1. Manufacturing Process of Oral Disintegrating Film 1.1 Preparation of HPMC Base:

Weighed quantity of hot purified water was taken in a beaker and slowly HPMC powder was added to it under continuous stirring, then purified water was to it and stir it for 7-10 minutes and kept aside for overnight for removing air bubbles.

1.2 Formulation:

1.2.1 Weighed quantity of purified water was taken in a beaker and paracetamol was added to it and stir it for 4-5 minutes, then sucralose was added to it and stir it for 4-5 minutes.

1.2.2 Weighed quantity of prosolve ODT G2 was added to step No. 1.2.1 and stir it for 4-5 minutes, then Hydroxypropyl-Betacyclodextrin was added to it and stir it for 2-3 minutes.

1.2.3 Weighed quantity of ammonium glycyrrhizinate was added to step No. 1.2.2 and stir it for 4-5 minutes, then xylitol was added to it and stir it for 7-10 minutes.

1.2.4 Weighed quantity of HPMC base was added to step No. 1.2.3 and sonicate it for 12-15 minutes, glycerol then was added to it and stir it for 7-10 minutes.

1.2.5 Weighed quantity of chocolate flavor was added to step No. 1.2.4 and stir it for 12-15 minutes, then cooling agent flavor was added to it and stir it for 12-15 minutes 1.2.6 Weighed quantity of sodium carbonate was added to step No. 1.2.5 and stir it for 12-15 minutes, then citric acid was added to it and stir it for 12-15 minutes, then solid choco color was added to it and stir it for 12-15 minutes and then kept aside for overnight for removing air bubbles.

Comparative Examples 1-5

Pharmaceutical compositions for oral film preparations were shown in Table-1. The pH values, bitter taste scores, were evaluated based on the following criteria.

Bitter taste score: 10 men and women aged 25 to 40 years were allowed to feel the taste of the compositions, the taste was scored based on the following criteria and those scores were averaged (the values were rounded off to two decimals).

0: No bitter taste
1: Tasteless
2: Bitter taste was perceptible
3: Slightly bitter taste was felt
4: Bitter taste was felt
5: Strong bitter taste was felt The compositions of Table 1 are not in scope of the claims

TABLE 1

| Ingredient | Comp Ex. 1 | Comp Ex. 2 | Comp Ex. 3 | Comp Ex. 4 | Comp Ex. 5 |
|---|---|---|---|---|---|
| Paracetamol | 120.0 | 120.0 | 120.0 | 120.0 | 120.0 |
| Hydroxypropyl methyl cellulose | 40.0 | 40.0 | 39.8 | 39.8 | 39.2 |
| Sucralose | 5.0 | 5.0 | 8.0 | 8.0 | 11.0 |
| Glycerol | 5.0 | 5.0 | 5.0 | 5.0 | 5.0 |
| Hydroxypropyl-β-cyclodextrin | 5.0 | 5.0 | 7.0 | 7.0 | 7.0 |
| Silicified microcrystalline cellulose | 0.0 | 18.0 | 21.0 | 21.0 | 22.0 |
| Chocolate flavor | 0.0 | 0.0 | 24.0 | 24.0 | 24.0 |
| Chocolate brown colour | 0.0 | 0.2 | 0.2 | 0.2 | 0.2 |
| Polo mint flavor | 0.0 | 0.0 | 0.0 | 10.0 | 10.0 |
| Xylitol | 0.0 | 0.0 | 0.0 | 0.0 | 4.6 |
| Purified water | Q.S | Q.S | Q.S | Q.S | Q.S |
| Total Solid Content | 175.0 | 193.2 | 225.0 | 235.0 | 243.0 |
| pH of the composition | 4.97 | 4.98 | 5.00 | 4.98 | 5.1 |
| Bitter taste score | 5.0 | 5.0 | 4.8 | 4.76 | 4.6 |

EXAMPLES 2-7

TABLE 2

| Ingredient | Ex. 2 | Ex. 3 | Ex. 4 | Ex. 5 | Ex. 6 | Ex. 7 |
|---|---|---|---|---|---|---|
| Paracetamol | 120.0 | 120.0 | 120.0 | 120.0 | 120.0 | 120.0 |
| Hydroxypropyl methyl cellulose | 39.2 | 39.6 | 49.0 | 49.0 | 48.6 | 48.6 |
| Sucralose | 11.0 | 11.0 | 11.0 | 11.0 | 11.0 | 11.0 |
| Glycerol | 5.0 | 5.0 | 5.0 | 5.0 | 5.0 | 5.0 |
| Hydroxypropyl-β-cyclodextrin | 7.0 | 7.0 | 7.0 | 7.0 | 7.0 | 7.0 |
| Silicified microcrystalline cellulose | 22.0 | 22.0 | 22.0 | 22.0 | 22.0 | 22.0 |
| Chocolate flavor | 24.0 | 24.0 | 24.0 | 24.0 | 24.0 | 24.0 |
| Chocolate brown colour | 0.2 | 0.2 | 0.2 | 0.2 | 0.2 | 0.2 |
| Polo mint flavor | 10.0 | 10.0 | 10.0 | 10.0 | 10.0 | 10.0 |
| Xylitol | 4.6 | 4.6 | 4.6 | 4.6 | 4.6 | 4.6 |
| Sodium Carbonate | 1.0 | 1.0 | 1.0 | 0.4 | 1.0 | 1.0 |
| Citric acid | 0.0 | 1.6 | 1.8 | 1.8 | 1.6 | 1.6 |
| Magnesium aluminometasilicate | 0.0 | 0.0 | 0.8 | 3.0 | 5.0 | 10.0 |
| Purified water | Q.S | Q.S | Q.S | Q.S | Q.S | Q.S |
| Total Solid Content | 244.0 | 246.0 | 255.8 | 258.0 | 260.0 | 265.0 |
| pH of the composition | 6.95 | 5.58 | 5.65 | 5.70 | 6.60 | 6.60 |
| Bitter taste score | 3.9 | 3.6 | 2.4 | 0.5 | 1.5 | 2.9 |
| Thickness of Film (mm) | 1.2 | 1.2 | 1.2 | 1.2 | 1.2 | 1.2 |
| Size of film (mm) | 32 × 32 | 32 × 32 | 32 × 32 | 32 × 32 | 32 × 32 | 32 × 32 |

As can be seen from table 2, when the mixture of sodium carbonate, citric acid and Magnesium aluminometasilicate are used in ratio of 1:4.5:7.5 (Example-5), the bitter taste of paracetamol was effectively masked. The composition of Example-5 comprises of 0.15% w/w of sodium carbonate, 0.7% w/w of citric acid and 1.2% of magnesium aluminometasilicate for which the taste of paracetamol was masked.

EXAMPLE 8

Dissolution

Dissolution profile of Example-5 was done in pH 1.2 Media (HCl Buffer), pH 4.5 Media (acetate buffer) and pH 6.8 Media (Phosphate buffer) in paddle apparatus at 50 RPM with volume of 900 mL and release profile is as depicted in Table-3.

TABLE 3

| Buffer Media | 5 minutes | 10 minutes | 15 minutes | 20 minutes | 30 minutes | 45 minutes |
|---|---|---|---|---|---|---|
| pH 1.2 | 72.0% | 100.0% | 103.0% | 103.0% | 103.0% | 103.0% |
| pH 4.5 | 43.0% | 59.0% | 70.0% | 77.0% | 86.0% | 93.0% |
| pH 6.8 | 50.0% | 83.0% | 99.0% | 103.0% | 104.0% | 104.0% |

I claim:

1. A fast dissolving film composition comprising
   a) paracetamol or pharmaceutically acceptable salt thereof;
   b) solubilizer selected from the group consisting of benzyl alcohol, hydroxypropyl-β-cyclodextrin, polyvinylpyrrolidone, and sulfobutylether-β-cyclodextrin;
   c) disintegrant selected from the group consisting of sodium starch glycolate, pregelatinized starch, carboxymethyl cellulose, and silicified microcrystalline cellulose; and
   d) taste masking agent; wherein taste masking agent is a mixture of sodium carbonate, citric acid and magnesium aluminometasilicate.

2. The fast dissolving film according to claim 1, wherein the ratio of solubilizer and disintegrant is of about 1:3 to about 3:1.

3. The fast dissolving film according to claim 1, wherein the ratio of sodium carbonate, citric acid and magnesium aluminometasilicate is of about 1:4.5:7.5.

4. The fast dissolving film according to claim 1, further comprising a polymer; wherein the paracetamol or pharmaceutically acceptable salt thereof is present in an amount of at least 100 mg or at least 40% w/w by weight based on the total weight of the composition and wherein polymer is selected from group consisting of hydroxypropyl methylcellulose, ethyl cellulose, hydroxypropyl cellulose, polyvinyl alcohol and cellulose acetate phthalate.

5. The fast dissolving film according to claim 1, further comprises a plasticizer selected from group consisting of polyethylene glycol, diethyl phthalate, propylene glycol and glycerol.

6. The fast dissolving film according to claim 1, further comprises a sweetening agent selected from the group consisting of aspartame, sucralose, dextrose, fructose, ammonium glycyrrhizinate, maltose, mannitol, sorbitol and xylitol.

7. The fast dissolving film according to claim 6, wherein the sweetening agent is a mixture of xylitol and sucralose in a ratio of about 3:1 to about 1:3.

8. A fast dissolving film composition comprising of
   a) at least 40% w/w of paracetamol; and
   b) taste masking agent; wherein taste masking agent is a mixture of sodium carbonate, citric acid and magnesium aluminometasilicate.

9. The fast dissolving composition according to claim 8, wherein the composition comprises of about 45.0% w/w to about 50.0% w/w paracetamol based on total weight of film composition and tasting masking agent mixture consisting about 0.1% w/w to about 0.5% w/w sodium carbonate, about 0.5% w/w to about 1.0 w/w citric acid and about 0.5% w/w to about 2.0% w/w magnesium aluminometasilicate based on total weight of film composition.

10. A fast dissolving film composition comprising of
   a) about 45.0% w/w to about 50.0% w/w paracetamol based on total weight of film composition;
   b) about 15.0% w/w to about 25.0% w/w hydroxypropyl methylcellulose based on total weight of film composition;
   c) about 1.0% w/w to about 5.0% w/w hydroxypropyl β-cyclodextrin based on total weight of film composition;
   d) about 5.0% w/w to about 10.0% w/w silicified microcrystalline cellulose based on total weight of film composition;
   e) tasting masking agent mixture consisting about 0.1% w/w to about 0.5% w/w sodium carbonate, about 0.5% w/w to about 1.0 w/w citric acid and about 0.5% w/w to about 2.0% w/w magnesium aluminometasilicate based on total weight of film composition;
   f) sweetening agent mixture consisting about 3% w/w to about 5% w/w sucralose and about 1.0% w/w to about 3% w/w of xylitol based on the total weight of film composition;
   g) about 1.0% w/w to about 5.0% w/w of glycerol based on the total weight of film composition; and
   h) at least one excipient selected from coloring agents and flavoring agents.

* * * * *